(12) United States Patent
Shipp (10) Patent No.: US 8,172,870 B2
(45) Date of Patent: May 8, 2012

(54) LIGATION CLIP APPLIER

(75) Inventor: John I. Shipp, Jacksonville Beach, FL (US)

(73) Assignee: Microline Surgical, Inc., Beverly, MA (US)

( * ) Notice: Subject to any disclaimer, the term of this patent is extended or adjusted under 35 U.S.C. 154(b) by 904 days.

(21) Appl. No.: 10/864,780

(22) Filed: Jun. 9, 2004
(Under 37 CFR 1.47)

(65) Prior Publication Data

US 2005/0119677 A1    Jun. 2, 2005

Related U.S. Application Data

(60) Provisional application No. 60/477,106, filed on Jun. 9, 2003, provisional application No. 60/513,518, filed on Oct. 21, 2003.

(51) Int. Cl.
*A61B 17/00* (2006.01)
(52) U.S. Cl. .................. 606/205; 606/139; 606/142
(58) Field of Classification Search .......... 606/151–158, 606/205–210, 139, 142–144
See application file for complete search history.

(56) References Cited

U.S. PATENT DOCUMENTS

| | | | |
|---|---|---|---|
| 648,841 A | 5/1900 | Brosnan | |
| 1,332,287 A | 3/1920 | Genevieve et al. | |
| 1,458,797 A | 6/1923 | Beale | |
| 1,668,514 A | 4/1928 | Sigler | |
| 2,113,991 A | 4/1938 | Larsen | |
| 2,489,372 A | 2/1950 | Kortlucke, Jr. et al. | |
| 2,628,608 A | 1/1953 | Garland | |
| 2,874,384 A | 2/1959 | Krone | |
| 2,876,778 A | 3/1959 | Kees, Jr. | |
| 3,023,039 A | 2/1962 | Henningsen et el. | |
| 3,023,468 A | 3/1962 | Hord et al. | |

(Continued)

FOREIGN PATENT DOCUMENTS

DE    2330182    1/1975

(Continued)

OTHER PUBLICATIONS

Papainoannou, Thanassis, M.S., Daykhovsky, Leon, M.D., Grundfest, Warren S., M.D.: "Safety Evaluation of Laproscopically Applied Clips": *Journal of Laparoscopic Surgery* 1996: 6(2): 99-106.

(Continued)

*Primary Examiner* — Gary Jackson
*Assistant Examiner* — Diane Yabut
(74) *Attorney, Agent, or Firm* — Greenblum & Bernstein, P.L.C.

(57) ABSTRACT

A ligation clip applicator design is provided that is particularly applicable to placement of a surgical ligation clip during a laparoscopic surgical procedure. The applicator has a magazine including first and second longitudinally extending partially closed channels within which enlarged portions of a ligation clip are received and held in an open position. First and second substantially parallel compression members are attached to the magazine and have first and second channel extensions therein aligned with the first and second channels of the magazine for receiving the first and second enlarged portions of the clip. The channel extensions include first and second releasing openings. The compression members close about a vessel, remaining substantially parallel as they close. The clip is pushed forward into the compression members to a position where the enlarged portions of the clip are aligned with the releasing openings, permitting the clip to be released to close and ligate the vessel.

18 Claims, 7 Drawing Sheets

U.S. PATENT DOCUMENTS

| | | |
|---|---|---|
| 3,032,039 A | 5/1962 | Beaty |
| 3,058,408 A | 10/1962 | Brown |
| 3,098,232 A | 7/1963 | Brown |
| 3,120,230 A | 2/1964 | Skold |
| 3,125,789 A | 3/1964 | Parker |
| 3,270,745 A | 9/1966 | Wood |
| 3,274,658 A | 9/1966 | Pile |
| 3,363,628 A | 1/1968 | Wood |
| 3,439,522 A | 4/1969 | Wood |
| 3,439,523 A | 4/1969 | Wood |
| 3,476,114 A | 11/1969 | Shannon et al. |
| 3,518,993 A | 7/1970 | Blake |
| 3,631,707 A | 1/1972 | Miller |
| 3,675,688 A | 7/1972 | Bryan et al. |
| 3,683,927 A | 8/1972 | Noiles |
| 3,757,629 A | 9/1973 | Schneider |
| 3,777,538 A | 12/1973 | Weatherly et al. |
| 3,827,277 A | 8/1974 | Weston |
| 3,827,438 A | 8/1974 | Kees, Jr. |
| 3,882,854 A | 5/1975 | Hulka et al. |
| 3,911,923 A | 10/1975 | Yoon |
| 3,955,581 A | 5/1976 | Spasiano et al. |
| 3,989,049 A | 11/1976 | Yoon |
| 4,017,337 A | 4/1977 | Winter et al. |
| 4,024,868 A | 5/1977 | Williams |
| 4,027,510 A | 6/1977 | Hiltebrandt |
| 4,038,987 A | 8/1977 | Komiya |
| 4,041,931 A | 8/1977 | Elliott et al. |
| 4,064,881 A | 12/1977 | Meredith |
| 4,086,926 A | 5/1978 | Green et al. |
| 4,146,130 A | 3/1979 | Samuels et al. |
| 4,152,920 A | 5/1979 | Green |
| 4,169,476 A | 10/1979 | Hiltebrandt |
| 4,170,990 A | 10/1979 | Baumgart et al. |
| 4,196,836 A | 4/1980 | Becht |
| 4,217,902 A | 8/1980 | March |
| 4,226,239 A | 10/1980 | Polk et al. |
| 4,226,242 A | 10/1980 | Jarvik |
| 4,228,895 A | 10/1980 | Larkin |
| 4,241,734 A | 12/1980 | Kandel et al. |
| 4,242,902 A | 1/1981 | Green |
| 4,246,903 A | 1/1981 | Larkin |
| 4,274,415 A | 6/1981 | Kanamoto et al. |
| 4,299,224 A * | 11/1981 | Noiles .................. 606/143 |
| 4,317,451 A | 3/1982 | Cerwin et al. |
| 4,340,061 A | 7/1982 | Kees, Jr. et al. |
| 4,349,028 A | 9/1982 | Green |
| 4,367,746 A | 1/1983 | Derechinsky |
| 4,372,316 A | 2/1983 | Blake, III et al. |
| 4,374,523 A | 2/1983 | Yoon |
| 4,396,139 A | 8/1983 | Hall et al. |
| 4,412,539 A | 11/1983 | Jarvik |
| 4,418,694 A | 12/1983 | Beroff et al. |
| 4,425,915 A | 1/1984 | Ivanov |
| 4,427,008 A | 1/1984 | Transue |
| 4,430,997 A | 2/1984 | DiGiovanni et al. |
| 4,433,689 A | 2/1984 | Von Zeppelin |
| 4,444,187 A | 4/1984 | Perlin |
| 4,448,193 A | 5/1984 | Ivanov |
| 4,449,530 A | 5/1984 | Bendel et al. |
| 4,450,839 A | 5/1984 | Transue |
| 4,450,840 A | 5/1984 | Mericle et al. |
| 4,471,766 A | 9/1984 | Terayama |
| 4,471,780 A | 9/1984 | Menges et al. |
| 4,476,865 A | 10/1984 | Failla et al. |
| 4,478,218 A | 10/1984 | Mericle |
| 4,478,220 A | 10/1984 | Di Giovanni et al. |
| 4,480,641 A | 11/1984 | Failla et al. |
| 4,485,816 A | 12/1984 | Krumme |
| 4,487,205 A | 12/1984 | Di Giovanni et al. |
| 4,492,232 A | 1/1985 | Green |
| 4,493,319 A | 1/1985 | Polk et al. |
| 4,500,024 A | 2/1985 | DiGiovanni et al. |
| 4,509,518 A | 4/1985 | McGarry et al. |
| 4,512,345 A | 4/1985 | Green |
| 4,527,562 A | 7/1985 | Mericle |
| 4,550,715 A | 11/1985 | Santangelo et al. |
| 4,556,058 A | 12/1985 | Green |
| 4,556,060 A | 12/1985 | Perlin |
| 4,557,263 A | 12/1985 | Green |
| 4,562,839 A | 1/1986 | Blake, III et al. |
| 4,569,346 A | 2/1986 | Poirier |
| 4,570,633 A | 2/1986 | Golden |
| 4,590,937 A | 5/1986 | Deniega |
| 4,616,650 A | 10/1986 | Green et al. |
| 4,616,651 A | 10/1986 | Golden |
| 4,620,541 A | 11/1986 | Gertzman et al. |
| 4,624,254 A | 11/1986 | McGarry et al. |
| 4,637,395 A | 1/1987 | Caspar et al. |
| 4,638,804 A | 1/1987 | Jewusiak |
| 4,646,741 A | 3/1987 | Smith |
| 4,658,822 A | 4/1987 | Kees, Jr. |
| 4,660,558 A | 4/1987 | Kees, Jr. |
| 4,662,373 A | 5/1987 | Montgomery et al. |
| 4,665,906 A | 5/1987 | Jervis |
| 4,671,278 A | 6/1987 | Chin |
| 4,674,504 A | 6/1987 | Klieman et al. |
| 4,696,396 A | 9/1987 | Samuels |
| 4,702,247 A | 10/1987 | Blake, III et al. |
| 4,708,688 A | 11/1987 | Lee |
| 4,712,549 A | 12/1987 | Peters et al. |
| 4,741,337 A | 5/1988 | Smith et al. |
| 4,765,335 A | 8/1988 | Schmidt et al. |
| 4,777,949 A | 10/1988 | Perlin |
| 4,777,950 A | 10/1988 | Kees, Jr. |
| 4,788,966 A | 12/1988 | Yoon |
| 4,791,707 A | 12/1988 | Tucker |
| 4,796,625 A | 1/1989 | Kees, Jr. |
| 4,796,627 A | 1/1989 | Tucker |
| 4,799,481 A | 1/1989 | Transue et al. |
| 4,821,721 A | 4/1989 | Chin et al. |
| 4,822,348 A | 4/1989 | Casey |
| 4,834,096 A | 5/1989 | Oh et al. |
| 4,844,066 A | 7/1989 | Stein |
| 4,854,317 A | 8/1989 | Braun |
| 4,858,608 A | 8/1989 | McGuilkin |
| 4,869,268 A | 9/1989 | Yoon |
| 4,919,152 A | 4/1990 | Ger |
| 4,934,364 A | 6/1990 | Green |
| 4,943,298 A | 7/1990 | Fujita et al. |
| 4,944,443 A | 7/1990 | Oddsen et al. |
| 4,950,258 A | 8/1990 | Kawai et al. |
| 4,961,743 A | 10/1990 | Kees, Jr. et al. |
| 4,966,603 A | 10/1990 | Focelle et al. |
| 4,967,949 A | 11/1990 | Sandhaus |
| 4,976,722 A | 12/1990 | Failla |
| 4,979,950 A | 12/1990 | Transue et al. |
| 4,983,176 A | 1/1991 | Cushman et al. |
| 5,002,563 A | 3/1991 | Pyka et al. |
| 5,026,379 A | 6/1991 | Yoon |
| 5,030,226 A | 7/1991 | Green et al. |
| 5,035,692 A | 7/1991 | Lyon et al. |
| 5,037,433 A | 8/1991 | Wilk et al. |
| 5,044,540 A | 9/1991 | Dulebohn |
| 5,053,045 A | 10/1991 | Schmidt et al. |
| 5,084,057 A | 1/1992 | Green et al. |
| 5,100,420 A | 3/1992 | Green et al. |
| 5,139,566 A | 8/1992 | Kimura et al. |
| 5,156,608 A | 10/1992 | Troidl et al. |
| 5,156,609 A | 10/1992 | Nakao et al. |
| 5,171,249 A | 12/1992 | Stefanchik et al. |
| 5,171,250 A | 12/1992 | Yoon |
| 5,190,203 A | 3/1993 | Rodak |
| 5,192,288 A | 3/1993 | Thompson et al. |
| 5,197,970 A | 3/1993 | Green et al. |
| 5,207,692 A | 5/1993 | Kraus et al. |
| 5,217,473 A | 6/1993 | Yoon |
| 5,242,456 A | 9/1993 | Nash et al. |
| 5,257,713 A | 11/1993 | Green et al. |
| 5,290,299 A | 3/1994 | Fain et al. |
| 5,300,081 A | 4/1994 | Young et al. |
| 5,340,360 A | 8/1994 | Stefanchik |
| 5,342,373 A | 8/1994 | Stefanchik et al. |
| 5,364,002 A | 11/1994 | Green et al. |
| 5,366,134 A | 11/1994 | Green et al. |
| 5,368,600 A | 11/1994 | Failla et al. |
| 5,383,880 A | 1/1995 | Hooven |

| | | | |
|---|---|---|---|
| 5,389,098 A | 2/1995 | Tsuruta et al. | |
| 5,395,381 A * | 3/1995 | Green et al. | 606/143 |
| 5,431,668 A | 7/1995 | Burbank, III et al. | |
| 5,431,689 A | 7/1995 | Weinberg et al. | |
| 5,439,468 A | 8/1995 | Schulze et al. | |
| 5,474,567 A | 12/1995 | Stefanchik et al. | |
| 5,487,746 A | 1/1996 | Yu et al. | |
| 5,501,693 A | 3/1996 | Gravener | |
| 5,509,920 A | 4/1996 | Phillips et al. | |
| 5,514,149 A | 5/1996 | Green et al. | |
| 5,527,318 A | 6/1996 | McGarry | |
| 5,527,319 A | 6/1996 | Green et al. | |
| D372,937 S | 8/1996 | Anders | |
| 5,542,949 A | 8/1996 | Yoon | |
| 5,547,474 A | 8/1996 | Kloeckl et al. | |
| 5,593,414 A | 1/1997 | Shipp et al. | |
| 5,601,573 A | 2/1997 | Fogelberg et al. | |
| 5,601,574 A | 2/1997 | Stefanchik et al. | |
| 5,620,452 A | 4/1997 | Yoon | |
| RE35,525 E | 6/1997 | Stefanchik et al. | |
| 5,653,720 A | 8/1997 | Johnson et al. | |
| 5,681,330 A | 10/1997 | Hughett et al. | |
| 5,695,502 A | 12/1997 | Pier et al. | |
| 5,700,270 A * | 12/1997 | Peyser et al. | 606/142 |
| 5,700,271 A | 12/1997 | Whitfield et al. | |
| 5,702,408 A | 12/1997 | Wales et al. | |
| 5,733,089 A * | 3/1998 | Albright | 414/226.02 |
| D401,626 S | 11/1998 | Shyu | |
| 5,833,700 A | 11/1998 | Fogelberg et al. | |
| 5,843,097 A * | 12/1998 | Mayenberger et al. | 606/143 |
| 5,849,019 A * | 12/1998 | Yoon | 606/157 |
| 5,855,590 A * | 1/1999 | Malecki et al. | 606/205 |
| 5,858,018 A | 1/1999 | Shipp et al. | |
| 5,897,565 A | 4/1999 | Foster | |
| 5,921,997 A | 7/1999 | Fogelberg et al. | |
| 5,935,381 A * | 8/1999 | Trokhan et al. | 162/109 |
| 5,993,465 A | 11/1999 | Shipp et al. | |
| 6,139,555 A * | 10/2000 | Hart et al. | 606/139 |
| 6,159,223 A | 12/2000 | Danks et al. | |
| 6,193,732 B1 | 2/2001 | Frantzen et al. | |
| 6,226,843 B1 | 5/2001 | Crainich | |
| 6,290,575 B1 | 9/2001 | Shipp | |
| 6,350,269 B1 * | 2/2002 | Shipp et al. | 606/143 |
| 6,464,710 B1 | 10/2002 | Foster | |
| 6,652,539 B2 | 11/2003 | Shipp et al. | |
| 6,652,545 B2 * | 11/2003 | Shipp et al. | 606/157 |
| 6,723,109 B2 * | 4/2004 | Solingen | 606/151 |

FOREIGN PATENT DOCUMENTS

| | | |
|---|---|---|
| DE | 3722311 | 1/1989 |
| DE | 3802851 | 8/1989 |
| DE | 4015562 | 11/1991 |
| JP | 6-237939 | 8/1994 |
| SU | 1389762 | 4/1988 |
| WO | WO 90/03763 | 94/1990 |

OTHER PUBLICATIONS

Nelson, Timothy M., M.D., Nakashima, Masanobu, M.D., Mulvihill, Sean J., M.D.: "How Secure Are Laproscopically Placed Clips? An In Vitro and In Vivo Study": *Arch Surg.* 1992: 127:718-720: pub. Dec. 8, 1991.

Arnaud, Jean-Pierre, M.D., Bergamaschi, Roberto, M.D.,: "Migration and Slipping of Metal Clips After Celioscopic Cholecystectomy": *Surgical Laproscopy & Endoscopy* 1993: 3(6): 487-488: pub. 1993 Raven Press, Ltd., New York.

Klein, R.D., Jessup, G., Ahari, F., Connolly, R.J., Schwaitzberg, S.D.: "Comparison of titanium and absorbable polymeric surgical clips for use in laproscopic cholecystectomy": *Surgical Endoscopy* 1994: pub. 1994 Springer-Verlag New York Inc.

* cited by examiner

LIGATION CLIP APPLIER

The present application claims the benefit of U.S. provisional Application No. 60/477,106, filed Jun. 9, 2003, and U.S. provisional Application No. 60/513,518, filed Oct. 21, 2003, the disclosures of which are incorporated herein by reference.

BACKGROUND OF THE INVENTION

1. Field of the Invention

The present invention relates generally to mechanical devices used in surgical procedures to obtain ligation or hemostasis, and more particularly, to low profile tools that can apply a pre-formed, spring loaded ligation clip used during surgery to clamp around a vessel or duct, such as the cystic duct, and thereby obtain ligation.

2. Description of the Prior Art

It will be appreciated by those skilled in the art that the use of ligation clips to control bleeding during surgical procedures is well known. As described, for example, in U.S. Pat. Nos. 4,976,722 and 4,979,950, prior art clips are generally formed of metal wire, usually a titanium alloy, having a "U-shaped" rectangular cross-section. Such prior art clips often include a grooved pattern machined into the inner or clamping surfaces of the clip, in an attempt to enhance the ability of the clip to remain in position after it is closed around the vessel. Application of the clip to the vessel is normally effected by means of a crushing action produced by a clip applier, such as disclosed in U.S. Pat. No. 5,030,226. Such crushing actions, of course, permanently deform the clips, making them difficult to remove or re-position.

Prior art surgical ligation clips have several inherent problems. For example, the force applied by the clip to the vessel can be variable and inconsistent from one clip to the next, because of the variation in crushing force applied to the clip by the user. Further, prior art clips have a tendency to slip off the end of the blood vessel stub (i.e., perpendicular to the axis of the vessel) to which it has been applied, because of the low coefficient of friction associated with the clip, and lack of adequate restraining force provided by the clip. Because of this, separation of the clip from the vessel to which it has been applied, after the wound has been closed, is not uncommon. A related problem found in the prior art is the fact that the ligating or restraining force offered by the crushed clip varies along the length of the clip, decreasing toward the open end. Thus, the section of the vessel near the open end of the clip can be inadequately ligated.

It is also common in the prior art to actually form and crush the clip only at the time of its application to the targeted blood vessel. It is often required that the vessels of 4 mm and larger diameter be ligated. Because most clips of the prior art have no spring action it is required that the inside clearance dimension of the clip, prior to crushing, be larger than the vessel. This does not lend itself to clip applier designs that will pass through small 5 mm trocars. The applier must be inserted through a trocar, placed through the patient's external tissues, and into the surgical field. Thus, prior art ligation clip appliers used in laparoscopic procedures typically consist of a 10 mm diameter clip applier that can fit only through a trocar having a 10 to 11 mm diameter entry port. Because one goal of laparoscopic surgery is to minimize the size of the entry wound, a surgical ligation clip and clip applier that can be used within a 5 mm or even a 2.5 mm diameter trocar port is highly desirable.

New minimally invasive surgical procedures and the need for less invasiveness for current procedures require the development of smaller and smaller devices. The harvesting of saphalous veins and certain cardiovascular procedures would benefit from reduced diameters trocars, below 3 mm diameter.

Figure 1:
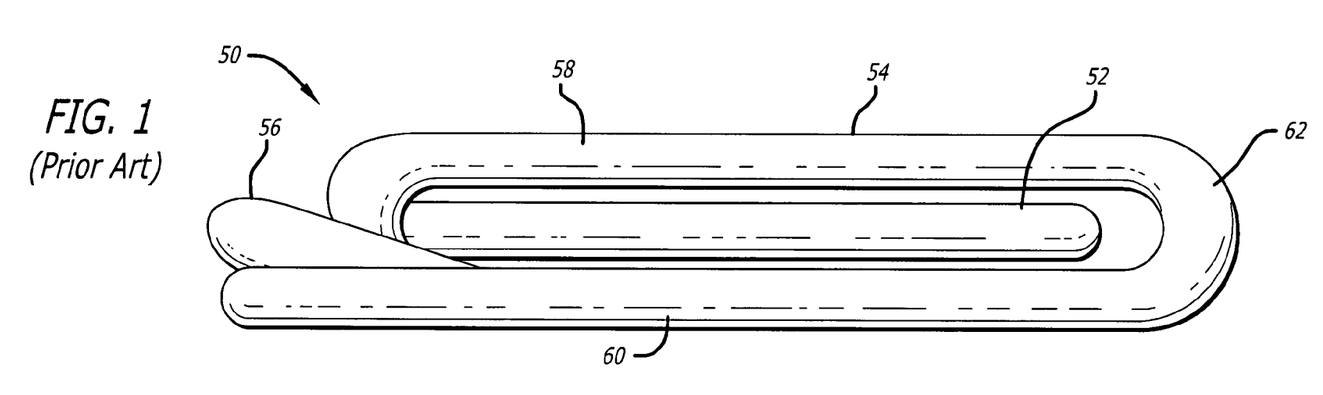
FIG. 1 is a top plan view of a surgical ligation clip disclosed in the prior art.
Figure 2:
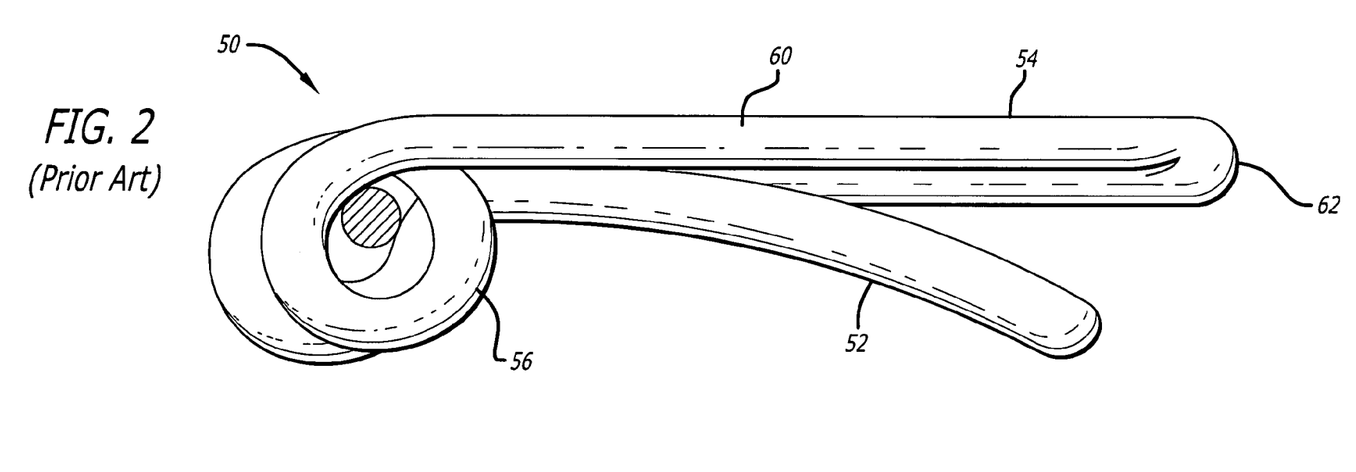
FIG. 2 is a side elevation view of the surgical ligation clip of FIG. 1.

To address these problems a spring action surgical clip was designed, and is disclosed in U.S. Pat. No. 5,593,414, titled "Method of Applying a Surgical Ligation Clip," the disclosure of which is incorporated herein by reference. One embodiment of the clip disclosed in the '414 patent is shown in FIGS. 1 and 2. Clip 50 has a vessel clamping arm 52, a vessel support member 54, and at least one tension coil 56 integrally joining the arm and support member. Clip 50 is pre-formed so that in its equilibrium state, it can be easily placed within the surgical field, including through an endoscopic trocar port with a diameter as little as 5 mm. After the clip is placed proximate the blood vessel or duct to be clamped, clamping arm 52 is moved from its equilibrium position to a position under higher tension, allowing positioning of the vessel between arm 52 and support member 54. When correct placement and positioning is achieved, arm 52 is released and, as the arm tends to move back towards its equilibrium position, it clamps the vessel between the arm's curved lower surface and the supporting upper surface of vessel support member 54.

To enhance the performance of the tension coil(s), vessel support member 54 includes first and second arms 58, 60, one of which terminates in a 180-degree bend section. Minimal cross-sectional area of the clip is achieved by substantially longitudinally aligning the vessel support member, the clamping arm, the 180-degree bend section 62, and the tension coil.

The clamping arm is pre-formed into an equilibrium that generally aligns with the horizontal plane of the support member. A second embodiment of the clip pre-loads the clamping arm into a pre-loaded equilibrium position where the free end of the arm rests against the upper surface of the support member.

There exists a relationship between the diameter of the trocar (hence the applier tube) and the maximum diameter of a vessel that can be ligated. Older crush clip technology limits the ratio of wound size to maximum diameter to be ligated to greater than 2. That is, to ligate a 5 mm vessel, a puncture wound of 10-12 mm is required. U.S. Pat. No. 5,593,414 teaches the method of using a spring clip that is inserted into the surgical field in the closed state, opened over a vessel, the diameter of which has been reduced, or pre-clamped, by the tool, and closed over the pre-clamped vessel. This method allows an entry wound to vessel diameter ratio of 1 or smaller. Thus, a 5 mm vessel can be ligated through a 5 mm trocar. This is substantially less invasive as compared to the older crush clip technology. For a trocar diameter of 2.5 mm, the clip can be scaled down to approximately half size on the wire diameter, coil height, and length, yet still supply an acceptable ligation force on a 2.5 mm vessel.

Unfortunately, several problems are encountered in applying the spring-action ligation clip of U.S. Pat. No. 5,593,414 to a vessel through a 5 mm or smaller trocar port. First, the nominal 5 mm cross-section of the clip that is inserted through the trocar places severe design restrictions on any applier mechanism. Second, care must be taken so that the elastic limit of the spring material is not exceeded when the clip is opened up so that it can be placed over the vessel diameter. For a titanium wire of diameter 0.75 mm, for example, lifting a distal end of a spring clip much above a few mm will exceed the elastic limit. Secondly, these spring clips are small and compact and owing to the preload, have a great deal of energy stored in the spring. As these clips are opened to place them over a vessel the stored energy increases substantially, in some cases more than doubling. This energy makes controlling the clip, to insure proper installation, difficult. Undesirable translation or rotation can result in misplacement or dropping of the clip inside the body.

Another approach which has been proposed to provide smaller diameter endoscopic clip application is that of U.S. Pat. No. 5,601,573 to Fogelberg et al. Fogelberg et al. still struggles with the complex manipulation required to advance the clip in a closed position and then open the clip prior to placement. Fogelberg et al. also has an overly complex multi-stage trigger arrangement for actuation of the jaws and the clip advancement mechanism. The present invention presents several improvements over Fogelberg et al. including: (1) advancement of the clips in their open position rather then a closed position; and (2) a smooth single stage trigger action which simultaneously closes the jaws and advances the forward most clip into the jaws. Another difference between the present invention and Fogelberg et al. is that Fogelberg et al. pushes a stack of clips, whereas the present invention individually engages and pushes each clip simultaneously, thus yielding better control of the clips.

The clip and clip applier disclosed in U.S. Pat. No. 6,350,269, titled "Ligation Clip and Clip Applier," the disclosure of which is incorporated herein by reference, represents a further improvement over the Fogelberg et al. device. The '269 patent discloses a clip having wire loops at one end thereof and a clip applier that utilizes the loop width to open and release the clip around a vessel.

There are several problems associated with the spring clip applicators of the prior art. First, the jaws are usually designed such that either one is stationary and the other rotates closed about the fixed jaw, or both jaws rotate in a scissor-like fashion about a common axis. This creates a severe pinching force on tissue that might be located near the axis or pivot point. This pinching force can cause a hematoma or otherwise damage the tissue. Secondly, the diverging surfaces of the jaws often obstruct the surgeon's view of the tissue to be ligated owing to the acute angle of the laparoscopic camera and the clip applier.

What is also needed is a clip applier with jaws that are substantially parallel to each other in an open position so that the surgeon has a better view of the tissue to be ligated.

SUMMARY OF THE INVENTION

In one preferred embodiment of the present invention, a surgical ligation apparatus for compressing a fluid carrying structure includes a proximal end, an opposite distal end, a mid-longitudinal axis passing through the proximal and distal ends, and a shaft having a passage adapted to receive at least one surgical ligation clip therein. The apparatus further includes upper and lower compression members proximate the distal end of the apparatus, each of the upper and lower compression members having a clamping surface for contacting the fluid carrying structure. The clamping surfaces each have a forward portion proximate the distal end of the apparatus and an opposite rearward portion. The rearward portions of the upper and lower clamping surfaces are moveable relative to one another a distance that is generally equal to a distance that the forward portions of the upper and lower clamping surfaces are moveable relative to one another to compress the fluid carrying structure between the clamping surfaces.

In another preferred embodiment of the present invention, a method of ligating a fluid carrying structure having a width includes inserting into a patient a surgical ligation instrument having upper and lower clamping surfaces moveable relative to one another between an open position for receiving the fluid carrying structure and a closed position for compressing the fluid carrying structure therebetween. The upper and lower clamping surfaces are adapted to contact the fluid carrying structure. The method further includes positioning the fluid carrying structure between clamping surfaces of the instrument; applying a substantially uniform compression across the width of the fluid carrying structure; moving a ligation clip over a portion of the clamping surfaces of the instrument, the ligation clip being resiliently biased to a closed position; and releasing the ligation clip to permit the ligation clip to move to the closed position.

These and other objects of the present invention will be apparent from review of the following specification and the accompanying drawings.

DETAILED DESCRIPTION OF THE PREFERRED EMBODIMENT

Reference will now be made in detail to the present preferred embodiments (exemplary embodiments) of the invention, examples of which are illustrated in the accompanying drawings.

Figure 3:
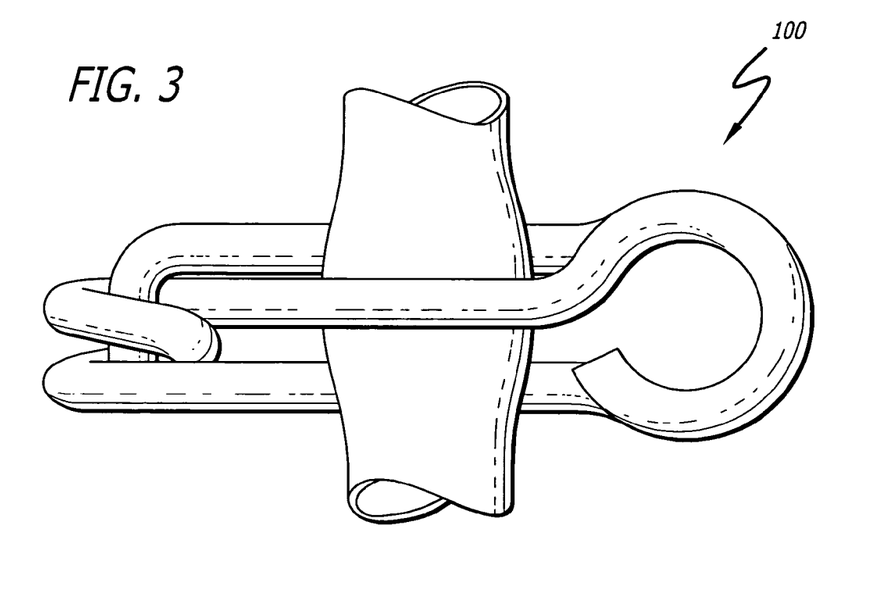
FIG. 3 is a top plan view of a surgical ligation clip in accordance with another embodiment of the present invention, the surgical ligation clip being engaged about a vessel.
Figure 4:
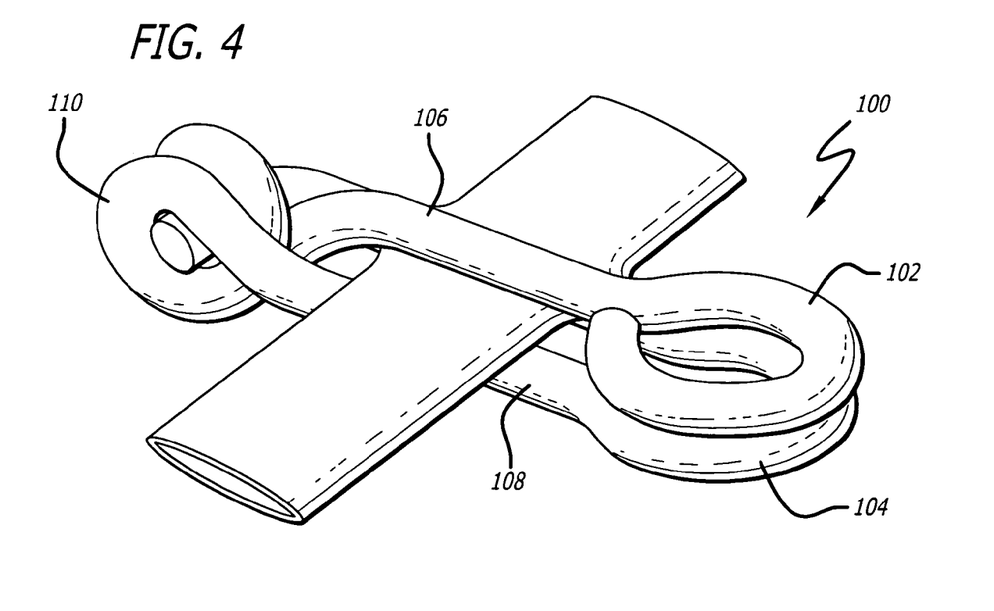
FIG. 4 is a perspective view of the surgical ligation clip of FIG. 3.

FIGS. 3 and 4 show an example of a surgical ligation clip 100 usable with a preferred embodiment of the clip applier of the present invention. Surgical ligation clip 100 includes a clamping arm 106 and a support member 108. A coil tension spring 110, which may also be generally referred to as a connector, joins clamping arm 106 and support member 108.

Clamping arm 106 has a first enlarged end 102 defined thereon. Support member 108 has a second enlarged end 104 defined thereon. The first and second enlarged ends 102, 104 are first and second wire loops which are integrally formed with clamping arm 106 and support member 108 of clip 100.

Figures 7, 8A:
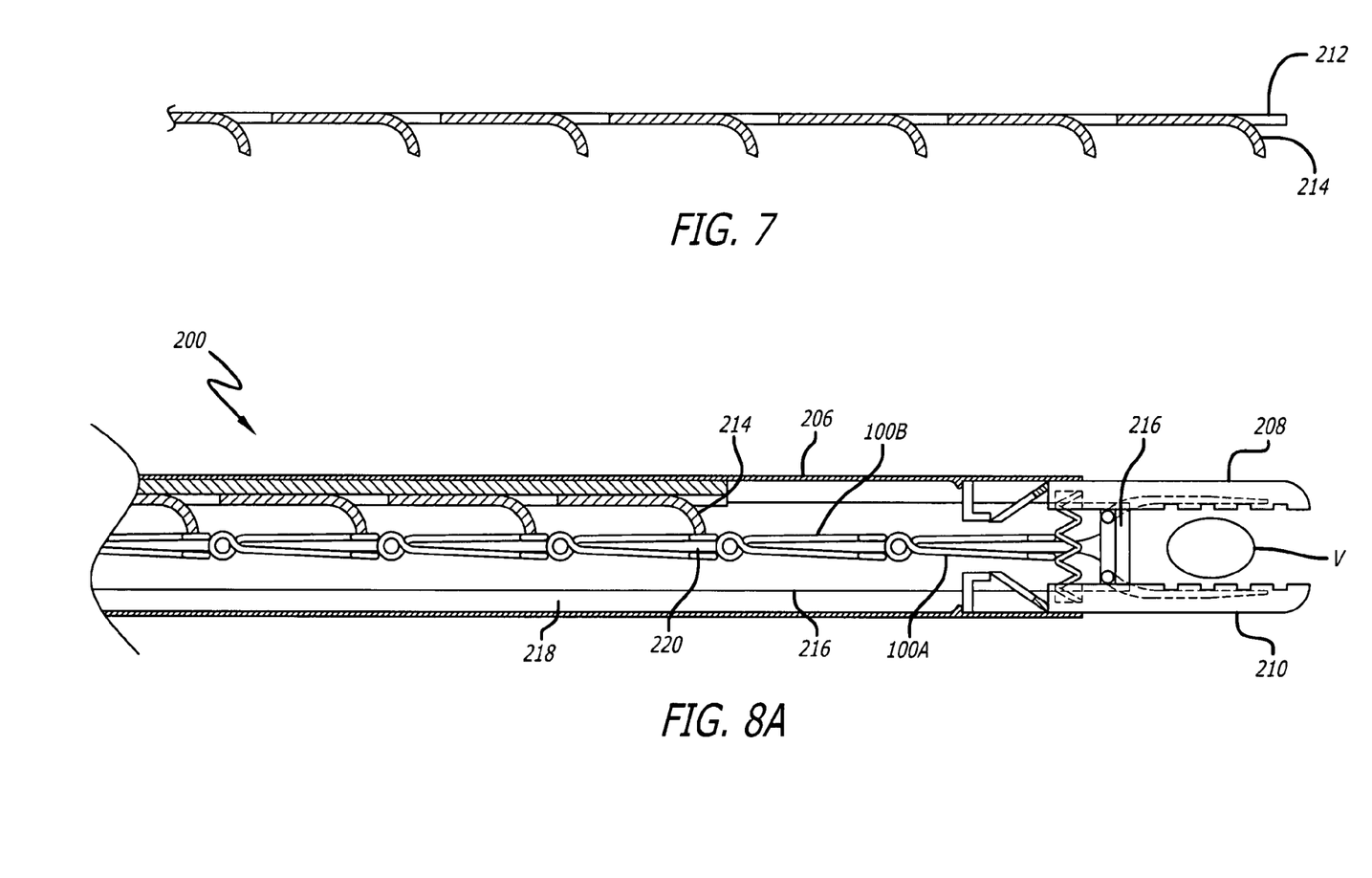
FIG. 7 is an enlarged view of a push rod for individually engaging a plurality of surgical ligation clips.
FIG. 8A is a partial side cross sectional view of the clip applier of FIG. 5.

Loops 102, 104, and particularly the laterally outer portions thereof, may be described as first and second control surfaces being received in and trapped within the first and second channels of a clip carrier 216. As best seen in FIG. 8A, a plurality of ligating clips 100 are received in clip carrier 216, in a semi-open position. For ease of identification, consecutive clips beginning with the forward-most one are designated as 100A, 100B, 100C, etc. The control surfaces, as engaged by the channels of clip carrier 216, prevent rotation and yawing of clip 100 as the clip is moved through the clip carrier.

The connector of clamping arm 106 and support member 108 is preferably a coil spring 110 which has a preload that biases the support member 108 and clamping arm 106 toward each other. The preload is preferably such that when clip 100 is in the fully closed or pre-loaded equilibrium position shown in FIG. 9B, there is still a spring preload in the connector which forces wire loops 102, 104 against each other.

Figure 5:
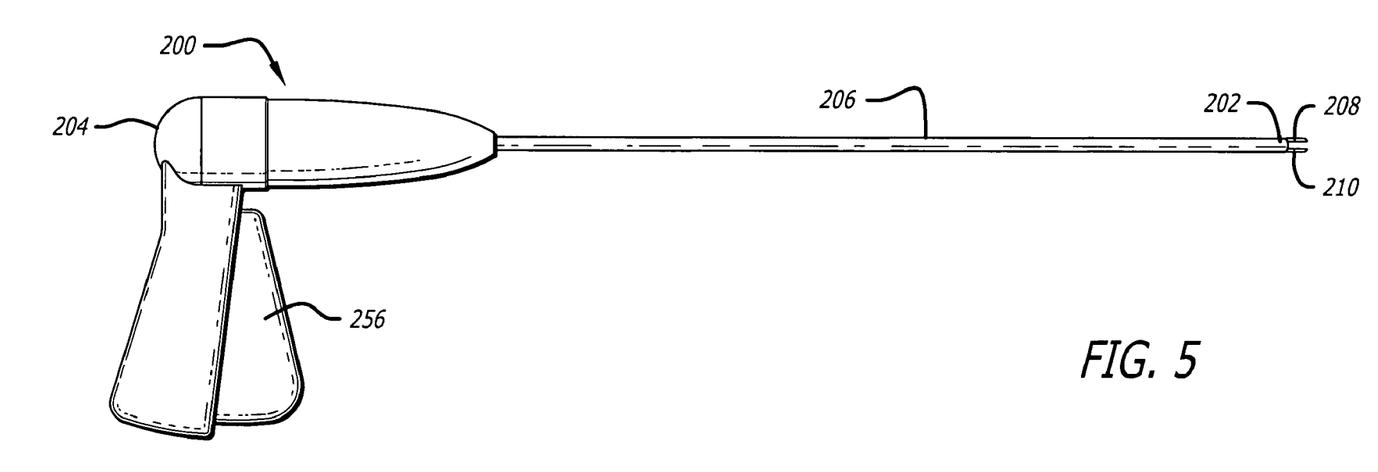
FIG. 5 is a side elevation view of a clip applier having a distal end with a pair of compression members in an open position in accordance with one embodiment of the present invention.
Figure 6:
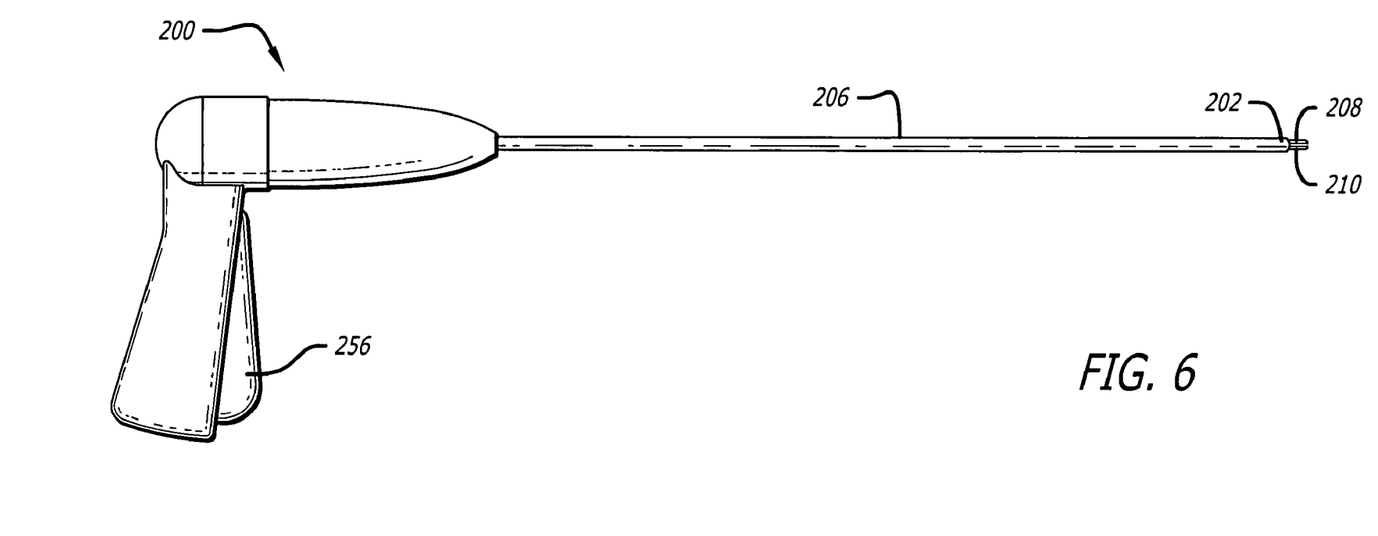
FIG. 6 is a side elevation view of the clip applier of FIG. 5 with the compression members in a closed position.

FIGS. 5 and 6 show one preferred embodiment of a clip applier 200 in accordance with the present invention. Clip applier 200 includes a distal end 202, a proximal end 204, and a tubular shaft 206 therebetween. Distal end 202 includes upper and lower compression members 208, 210 that are moveable between an open position, shown in FIG. 5, and a closed position, shown in FIG. 6.

FIG. 7 shows a pusher rod 212 which has a plurality of prongs 214 extending therefrom for engagement with clips 100 contained in a clip carrier 216 as seen in FIG. 8A. Pusher rod 212 is preferably an elongated flat bar. Pusher rod 212 is slidably received in a channel within passage 218 of shaft 206.

Figures 8B, 8C:
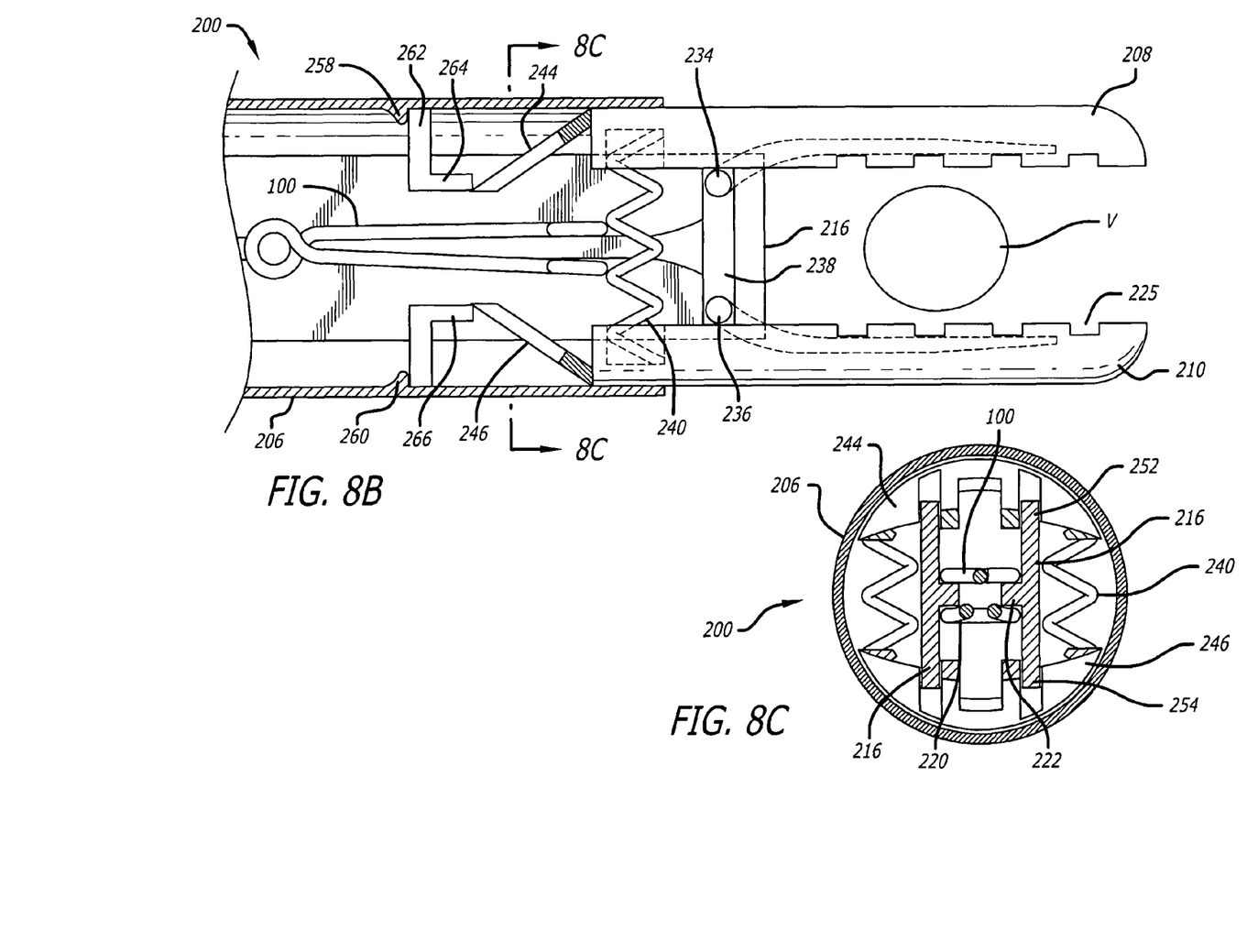
FIG. 8B is an enlarged fragmentary cross sectional view of the distal end of the clip applier of FIG. 8A.
FIG. 8C is a cross sectional view along line 8C-8C of FIG. 8B.

As shown in FIGS. 8A and 8C, clip carrier 216 includes a pair of opposed rails 220, 222 projecting from the interior sides of the clip carrier which define partially closed upper and lower channels. Rails 220, 222 extend along the length of clip carrier 216 and are configured to maintain clips 100 in a slightly open position as they are moved along the length of clip carrier 216 and into engagement with compression members 208, 210.

Figure 10:
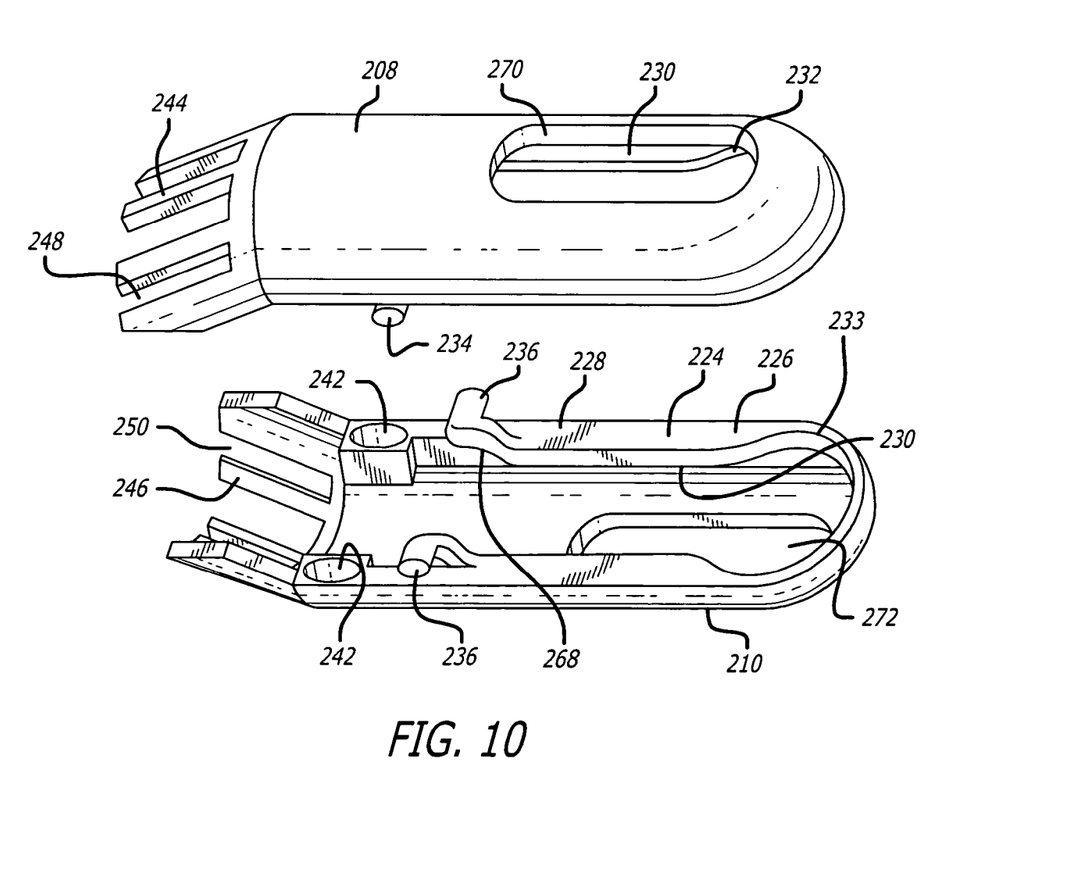
FIG. 10 is an exploded perspective view of the upper and lower compression members of the clip applier of FIG. 5.

FIG. 10 shows upper and lower compression members 208, 210. Compression members 208, 210 each include a clamping surface 224 configured to contact a fluid carrying structure. Clamping surface 224 includes a forward portion 226 proximate the distal end of the compression member and a rearward portion 228. If desired, clamping surface 224 may include a plurality of grooves and ridges 225 along the length of the clamping surface to provide additional grip. Upper and lower compression members 208, 210 also include an extension rail 230 vertically opposite clamping surface 224 that leads to a loop releasing openings 232, 233. The exterior surface of the forward end of each compression member is preferably blunt-shaped to minimize interference with surrounding tissue structures.

Figure 9A:
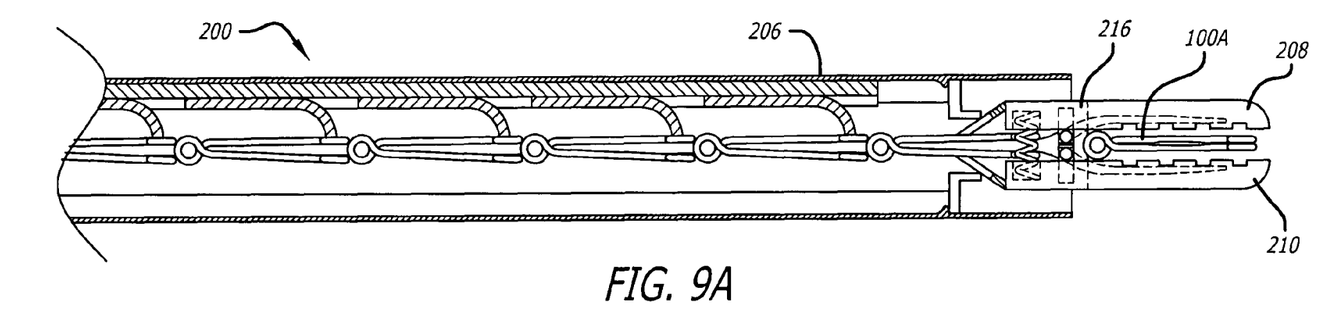
FIG. 9A is a partial side cross sectional view of the clip applier after discharging the clip.
Figure 9B:
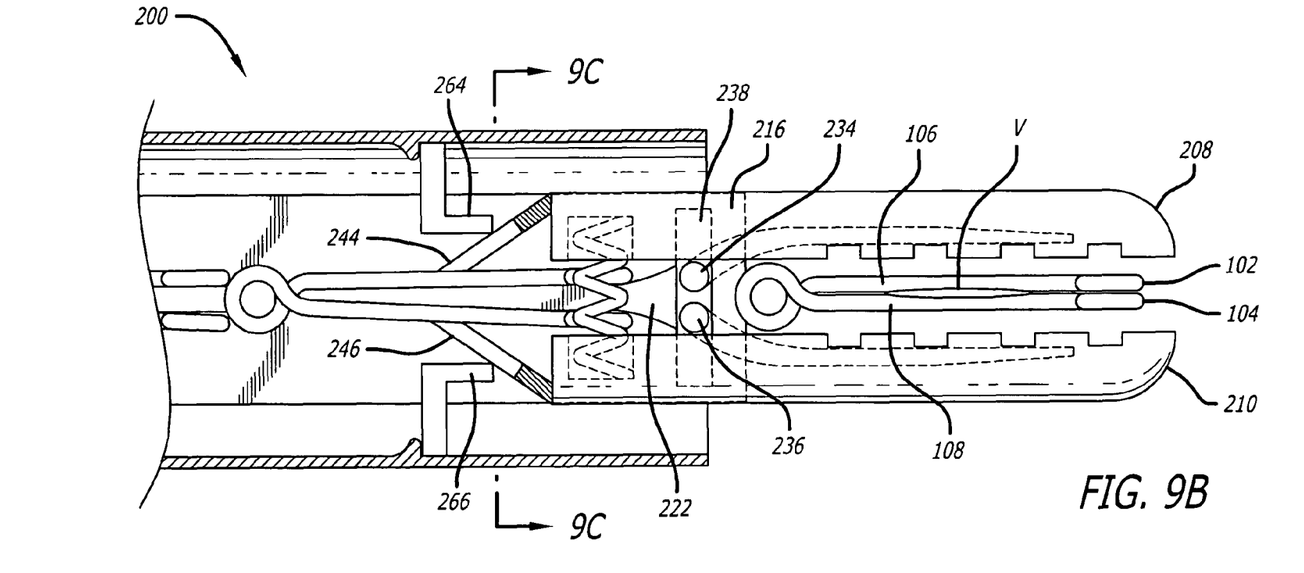
FIG. 9B is an enlarged fragmentary cross sectional view of the distal end of the clip applier of FIG. 9A.
Figure 9C:
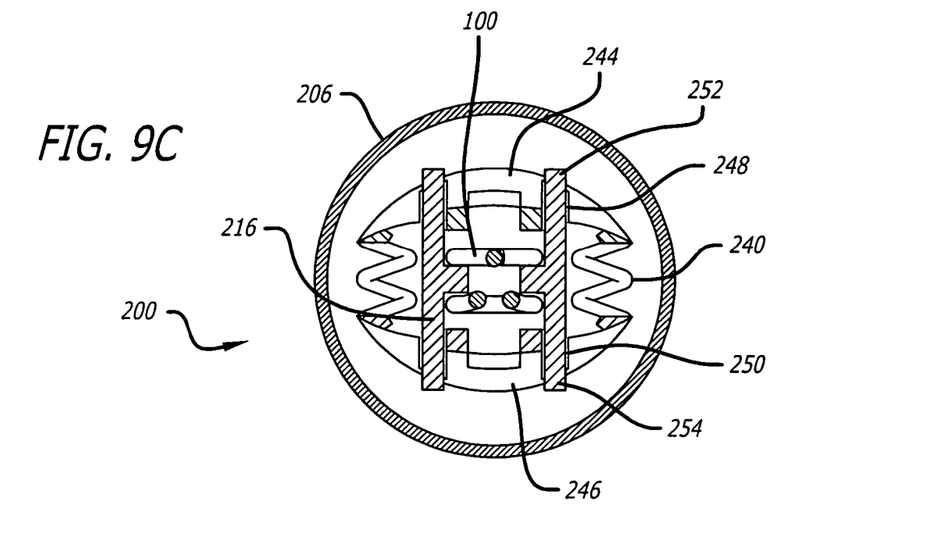
FIG. 9C is a cross sectional view along line 9C-9C of FIG. 9B.

Upper and lower compression members 208, 210 are attached to the distal end of clip carrier 216 by a pair of laterally extending pins 234, 236, respectively. Pins 234, 236 are configured for engagement with a slot 238 positioned proximate the distal end of clip carrier 216 in the interior sidewall of the clip carrier. Upper and lower compression members 208, 210 are biased to an open position by a pair of springs 240 receivable in spring receiving openings 242. The proximal end of each of upper and lower compression members 208, 210 include a ramp 244, 246, respectively. Ramps 244, 246 each include longitudinal recesses 248, 250, respectively, configured to receive portions 252, 254, respectively, of clip carrier 216 as shown in FIGS. 8C and 9C.

With reference to FIGS. 8A-8C and 9A-9C, the operation of clip applier 200 will now be described. FIGS. 6 and 8A-8C show clip applier 200 with upper and lower compression members 208, 210 in the open position. After a surgeon has inserted clip applier 200 through a trocar and into a patient, the surgeon positions a fluid carrying structure such as a vessel V or stub end of a tissue between upper and lower compression members 208, 210. Squeezing trigger 256 on the handle of clip applier 200 will cause shaft 206 to move forward relative to clip carrier 216 and upper and lower compression members 208, 210. At the same time, crimp features 258, 260, located on the interior wall of passage 218 of shaft 206, advance guide 262 forward with shaft 206. Trigger 256 is preferably a two-stage trigger so that a first squeeze will pre-clamp vessel V, as will be described below, and a continued second squeeze of trigger 256 will discharge clip 100. A two-stage trigger permits the surgeon the opportunity to evaluate whether vessel V is sufficiently pre-clamped before discharging a clip. It will be appreciated by those skilled in the art that other trigger actuation mechanisms are within the scope of the present invention and that a two-stage trigger is only a preferred embodiment of the present invention.

Guide 262 preferably has a circular outer diameter to match the interior diameter of passage 218. Guide 262 has a central opening configured to permit passage of clip 100 therethrough and is defined at least in part by upper and lower guide surfaces 264, 266, which are configured to move, preferably slide, against upper and lower ramps 244, 246 of upper and lower compression members 208, 210, respectively, as shown in FIGS. 8B and 9B. The central opening of guide 262 is preferably generally curved to match the curve of each of upper and lower ramps 246, 248 (see FIG. 8C).

As guide 262 moves forward along the mid-longitudinal axis of clip applier 200, ramps 244, 246 slide against guide surfaces 264, 266, forcing an inward motion of upper and lower compression members 208, 210 toward one another. Laterally extending pins 234, 236 of upper and lower compression members 208, 210, respectively, slide within slot 238 of clip carrier 216, which acts as a guide surface for pins 234, 236 and maintains the horizontal parallel alignment of upper and lower compression members 208, 210 while the upper and lower compression members move toward each other. The inward force caused by guide 262 sliding against ramps 244, 246 overcomes the biasing force provided by springs 240, which acts to keep upper and lower compression members 208, 210 in an open position. As would be appreciated by those skilled in the art, the length and slope of upper and lower ramps 244, 246 may be modified according to the dimensions of the clip to be used with the clip applier.

The forward-most clip 100A is pushed out of clip carrier 216 into upper and lower compression members 208, 210 by the next adjacent clip 10B. As forward-most clip 100A is pushed forward, the lateral sides of wire loops 102, 104 slide along rails 220, 222 of clip carrier 216 in a semi-open position owing to the biasing force towards the closed position of clip 100A against each rail. Continued forward movement of clip 100 along the length of the clip applier brings the lateral sides of wire loops 102, 104 up a ramped portion of rails 220, 222, over a ramp portion 268 of pins 234, 236, and onto rail extension 230 within upper and lower compression members 208, 210 (shown in FIG. 10). As wire loops 102, 104 come into registry with releasing openings 232, 233, support member 106 and clamping arm 108 of clip 100A snap shut toward each other, thus clamping vessel V therebetween as clip 100A is released from upper and lower compression members 208, 210, as shown in FIGS. 9A-9C. The surgeon can view the discharge of the clip through windows 270, 272 in upper and lower compression members 208, 210, respectively.

After trigger 256 has been squeezed to close compression members 208, 210 and advance clip 100A into the compression members where it is released, subsequent release of trigger 256 will pull back push rod 212. The column of clips 100 will stay in place within clip carrier 216 due to the gripping of rails 220, 222 by clips 100. Prongs 214 will slip back past the clips and engage the next rearward clip on the next squeeze of trigger 256.

When upper and lower compression members 208, 210 are closed together, a generally uniform vertical force is applied across the width of vessel V to occlude the vessel. The closing motion of compression members 208, 210 may be described as pre-clamping vessel V by movement of clamping surfaces 224 toward one another.

It is noted that the step of pre-clamping vessel V between upper and lower compression members 208, 210 typically occurs prior to the step of pushing spring clip 100A from clip carrier 216 into upper and lower compression members 208, 210. As spring clip 100A is moved into upper and lower compression members 208, 210, it subsequently is released from those compression members when the wire loops move into registry with the releasing openings 232, 233.

It is further noted that the methods of operating clip applier 200 includes steps of loading in a plurality of spring clips 100 into clip carrier 216 such that the wire loops 102, 104 are received within channels with the clips thus held in an open position by rails 220, 222. Then, each time that trigger 256 is compressed, each clip 100 is advanced forward in clip carrier 216. Clips 100 are arranged in clip carrier 216 head to tail with a small space between adjacent clips so that the clips are pushed through clip carrier 216 by prongs 214 of pusher rod 212.

During this procedure rotation of spring clip 100 is prevented by containing wire loops 102, 104 in the partially closed channels of clip carrier 216.

In summary, compression members 208, 210 are substantially parallel and are fixedly attached to the applier at slidable pins 234, 236. Slidable pins 234, 236 engage clip magazine 216 in slot 238. Magazine 216 is fixedly attached to the handle of the applier. Tubular shaft 206 is distally movable during the trigger stroke. As tubular shaft 206 moves distally under the control of the trigger stroke, crimp features 258, 260 cause guide 262 to move distally. Protrusions 264, 266 move up ramps 244, 246 that are fixedly attached to upper and lower compression members 208, 210. This force has a downward component that compresses spring 240 and moves upper and lower compression members 208, 210 toward each other, compressing tissue therebetween. Pins 234, 236 ride in slot 238 keeping upper and lower compression members 208, 210 registered with each other and substantially parallel, as shown in FIGS. 8B and 9B. In the second part of the trigger stroke, the spring clip, which has control features mating with rails 220, 222, rides up onto pins 234, 236 and onto upper and lower compression members 208, 210. Ejection and tissue ligation then occurs.

With this invention there is thus no jaw pivot to damage tissue. In addition, since the compression members are substantially parallel to one another, visibility is enhanced.

It will be appreciated by those skilled in the art that the embodiment described above is only exemplary and that the clip applier of the present invention may be modified without going beyond the scope of the present invention. For example, although two springs are shown on each side of the proximal end of the compression members, a single spring or other mechanical equivalents may be used to bias the compression members if it is desired that the compression members be biased relative to one another. Movement of the upper and lower compression members toward one another may be accomplished in other ways such as with a vertical turn screw and gear arrangement. The compression members may be directly attached to the shaft of the clip applier rather than the clip carrier as would be appreciated by those skilled in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A ligation clip and a surgical ligation apparatus in combination with one another for compressing a fluid carrying structure, said ligation clip comprising a clamping arm and a support member biased toward one another, wherein said surgical ligation apparatus positions said ligation clip so that the fluid carrying structure is received between said clamping arm and said support member; and said surgical ligation apparatus comprising:

a proximal end, an opposite distal end, and a mid-longitudinal axis passing through said proximal and distal ends;

a shaft having a passage adapted to receive at least one said surgical ligation clip therein;

upper and lower compression members proximate said distal end of said apparatus, each of said upper and lower compression members having a clamping surface for contacting the fluid carrying structure, and a longitudinal axis, said clamping surfaces being substantially parallel to one another in an open position, said clamping surfaces each having a forward portion proximate said distal end of said apparatus and an opposite rearward portion, and said upper and lower compression members being non-pivotably moveable relative to one another, said rearward portions of said upper and lower clamping surfaces being moveable relative to one another a distance that is generally equal to a distance that said forward portions of said upper and lower clamping surfaces are moveable relative to one another to compress the fluid carrying structure between said clamping surfaces, wherein said upper and lower compression members each include a first guide surface on the proximalmost portions thereof; and an actuating system adapted to move said upper and lower compression members toward each other so that the longitudinal axes of said upper and lower compression members remain substantially parallel to one another and to the mid-longitudinal axis of said surgical ligation apparatus, said actuating system including a second guide surface configured to move against the first guide surfaces of said upper and lower compression members to move said upper and lower compression members toward each other.

2. The apparatus of claim 1, wherein said upper and lower compression members each move relative to the mid-longitudinal axis of said apparatus.

3. The apparatus of claim 1, wherein said upper and lower compression members are biased to the open position for receiving the fluid carrying structure therebetween.

4. The apparatus of claim 1, further comprising a spring adapted to bias said upper and lower compression members to the open position for receiving the fluid carrying structure therebetween.

5. The apparatus of claim 1, wherein said clamping surfaces of said upper and lower members include a plurality of ridges and grooves to frictionally hold the fluid carrying structure.

6. The apparatus of claim 1, further comprising a clip carrier moveable within said passage of said shaft for holding a plurality of surgical ligation clips therein, said clip carrier having a proximal end and an opposite distal end.

7. The apparatus of claim 6, wherein said clip carrier includes a guide surface for maintaining substantially vertical movement of said upper and lower compression members relative to one another.

8. The apparatus of claim 1, further comprising a pair of springs, each spring of the pair of springs disposed between the upper and lower compression members and arranged to receive said at least one surgical ligation clip between the pair of springs.

9. A surgical ligation clip and a surgical ligation apparatus in combination with one another for compressing a fluid carrying structure,
   said surgical ligation clip comprising a clamping arm and a support member biased toward one another, wherein said surgical ligation apparatus positions said surgical ligation clip so that the fluid carrying structure is received between said clamping arm and said support member; and
   said surgical ligation apparatus comprising:
      a proximal end, an opposite distal end, and a mid-longitudinal axis passing through said proximal and distal ends;
      a shaft having a passage adapted to receive said surgical ligation clip therein; and
      upper and lower compression members proximate said distal end of said apparatus, said upper and lower compression members each having a clamping surface for contacting the fluid carrying structure, a longitudinal axis, and being non-pivotably moveable relative to one another so that the longitudinal axes of said upper and lower compression members remain substantially parallel to one another and to the mid-longitudinal axis of said surgical ligation apparatus, said clamping surfaces being substantially parallel to one another in an open position, and said upper and lower compression members each having a guide surface for guiding said surgical ligation clip over at least a portion of the fluid carrying structure, and said upper and lower compression members each further having a first guide surface on the proximalmost portions thereof and configured such that a second guide surface is movable against the first guide surfaces to relatively move said upper and lower compression members.

10. The apparatus of claim 9, wherein said upper and lower compression members are biased to the open position for receiving the fluid carrying structure therebetween.

11. The apparatus of claim 9, further comprising a pair of springs, each spring of the pair of springs disposed between the upper and lower compression members and arranged to receive said at least one surgical ligation clip between the pair of springs.

12. A method of ligating a fluid carrying structure, the method comprising the steps of:
   inserting into a patient a surgical ligation instrument having an upper compression member with a longitudinal axis and an upper clamping surface and a lower compression member with a longitudinal axis and a lower clamping surface, the upper and lower compression members being moveable relative to one another between an open position for receiving the fluid carrying structure and a closed position for compressing the fluid carrying structure therebetween, and the upper and lower clamping surfaces being adapted to contact the fluid carrying structure;
   positioning the fluid carrying structure between clamping surfaces of the instrument;
   moving the upper and lower compression members and the clamping surfaces thereof toward a mid-longitudinal axis of the instrument from the open position, where the longitudinal axes are disposed at a first angle relative to one another and the upper and lower clamping surfaces are substantially parallel to one another, to the closed position, where the longitudinal axes are disposed at a second angle relative to one another generally equal to the first angle and the upper and lower clamping surfaces are substantially parallel to one another, wherein said moving the upper and lower compression members is effected by first guide surfaces on the proximalmost portions of each of the upper and lower compression members being contacted and moved by respective second guide surfaces of the instrument;
   maintaining the substantially parallel orientation of the upper and lower clamping surfaces during movement of the upper and lower compression members from the open position to the closed position;
   moving a ligation clip through at least a portion of the instrument and then over a portion of the clamping surfaces of the instrument, the ligation clip being resiliently biased to a closed position; and
   releasing the ligation clip to permit the ligation clip to move to the closed position.

13. The method of claim 12, wherein the step of moving the upper and lower compression members includes moving the clamping surfaces toward a proximal end of the instrument.

14. The method of claim 12, wherein the upper and lower clamping surfaces each have a forward portion and a rearward portion, the step of moving the upper and lower compression members including moving the forward and rearward portions of the upper and lower clamping surfaces toward each other a generally equal distance.

15. The method of claim 12, wherein the step of moving includes opening the ligation clip to a maximum open position prior to moving the clip over the clamping surfaces.

16. The method of claim 12, further comprising the step of inserting a clip carrier into a passage of the instrument, the clip carrier being adapted to hold a plurality of surgical ligation clips.

17. The method of claim 12, wherein the ligation clip includes a clamping arm and a support arm biased toward one another for receiving the fluid carrying structure therebetween.

18. The method of claim 12, further comprising moving the ligation clip between a pair of pair of springs disposed between the upper and lower compression members.

* * * * *